(12) United States Patent
Yamaguchi

(10) Patent No.: US 9,797,839 B2
(45) Date of Patent: Oct. 24, 2017

(54) SYSTEM FOR APPLYING PHANTOM SAMPLE TO EVALUATE OPTICAL ANALYSIS DEVICE, STORAGE DEVICE STORING INSTRUCTIONS, METHOD AND PHANTOM SAMPLE

(71) Applicant: OLYMPUS CORPORATION, Tokyo (JP)

(72) Inventor: Mitsushiro Yamaguchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 69 days.

(21) Appl. No.: 14/738,134

(22) Filed: Jun. 12, 2015

(65) Prior Publication Data

US 2015/0355092 A1    Dec. 10, 2015

Related U.S. Application Data

(63) Continuation of application No. PCT/JP2013/076801, filed on Oct. 2, 2013.

(30) Foreign Application Priority Data

Mar. 13, 2013  (JP) .................................. 2013-050775

(51) Int. Cl.
*G01D 18/00* (2006.01)
*G01N 21/64* (2006.01)
(Continued)

(52) U.S. Cl.
CPC ........... *G01N 21/645* (2013.01); *G01M 11/00* (2013.01); *G01M 11/02* (2013.01); *G01N 21/274* (2013.01);
(Continued)

(58) Field of Classification Search
CPC ... G01N 21/276; G01N 21/278; G01N 21/274
See application file for complete search history.

(56) References Cited

U.S. PATENT DOCUMENTS 6,794,424 B2 * 9/2004 Holcomb ............. G01N 21/278
523/137
2004/0012676 A1 * 1/2004 Weiner ................. G01N 21/253
348/207.1
(Continued)

FOREIGN PATENT DOCUMENTS

JP    2005-098876 A    4/2005
JP    3706367 B2    10/2005
(Continued)

OTHER PUBLICATIONS

"Calibration of Fluorescence Microscopes" G.I.T. Imaging & Microscopy Mar. 2013, pp. 41-43, to Verlag GmbH (Mar. 2013).*
(Continued)

*Primary Examiner* — Kenneth J Malkowski
(74) *Attorney, Agent, or Firm* — Scully, Scott, Murphy & Presser, P.C.

(57) ABSTRACT

An optical system of an optical analysis device is easily evaluated with high accuracy.
There is provided a method of evaluating an optical analysis device including an optical system A capable of forming a confocal volume C at a focal position by condensing excitation light B, the method including the steps of: placing, at the focal position of the optical system A, a phantom sample in which two or more types of solid members having different fluorescent substance concentrations are arranged adjacent to each other; irradiating the phantom sample 1 with excitation light through the optical system A while relatively moving the confocal volume C formed by the optical system A and the phantom sample in an arrangement direction of the solid members; detecting fluorescent light
(Continued)

generated in the solid members placed in the confocal volume C; and evaluating the optical system A based on the detected fluorescent light.

19 Claims, 4 Drawing Sheets

(51) Int. Cl.
*G01M 11/00* (2006.01)
*G01N 21/27* (2006.01)
*G02B 21/00* (2006.01)
*G02B 21/34* (2006.01)
*G01M 11/02* (2006.01)

(52) U.S. Cl.
CPC ....... *G01N 21/276* (2013.01); *G01N 21/6458* (2013.01); *G02B 21/008* (2013.01); *G02B 21/0076* (2013.01); *G02B 21/34* (2013.01); *G01N 21/278* (2013.01); *G01N 2201/06113* (2013.01); *G01N 2201/127* (2013.01); *G01N 2201/13* (2013.01)

(56) References Cited

U.S. PATENT DOCUMENTS

| | | |
|---|---|---|
| 2004/0051050 A1 | 3/2004 | Schmid et al. |
| 2004/0196455 A1 | 10/2004 | Ermantraut et al. |
| 2005/0030601 A1 | 2/2005 | Smith et al. |
| 2007/0159624 A1 | 7/2007 | Resch-Genger et al. |
| 2008/0137938 A1 | 6/2008 | Zahniser |
| 2009/0224174 A1* | 9/2009 | Netz ................. G01M 11/0264 250/459.1 |
| 2012/0227478 A1 | 9/2012 | Mukai et al. |

FOREIGN PATENT DOCUMENTS

| | | |
|---|---|---|
| JP | 4091437 B2 | 5/2008 |
| JP | 2010-512545 A | 4/2010 |
| JP | 4887494 B2 | 2/2012 |
| JP | 2012-189322 A | 10/2012 |
| JP | 2012-226055 A | 11/2012 |
| WO | WO 2011/108369 A1 | 9/2011 |

OTHER PUBLICATIONS

International Search Report dated Dec. 17, 2013 issued in PCT/JP2013/076801.
Resolution Test Targets, THORLABS, retrieved from Internet: http://www.thorlabs.co.jp/newgrouppage9.cfm?objectgroup_id=4338 on Apr. 7, 2015.
Extended Supplementary European Search Report dated Oct. 12, 2016 in European Patent Application No. 13 87 8233.9.
Groen, Frans C.A. et al., "A Comparison of Different Focus Functions for Use in Autofocus Algorithms", Cytometry, Mar. 1, 1985, vol. 6, No. 2, pp. 81-91.

* cited by examiner

SYSTEM FOR APPLYING PHANTOM SAMPLE TO EVALUATE OPTICAL ANALYSIS DEVICE, STORAGE DEVICE STORING INSTRUCTIONS, METHOD AND PHANTOM SAMPLE

CROSS-REFERENCE TO RELATED APPLICATIONS

This application is a continuation of International Application No. PCT/JP2013/076801 filed on Oct. 2, 2013, which claims priority to Japanese Patent Application No. JP 2013-050775 filed on Mar. 13, 2013, the entire contents of each of which is incorporated herein by reference.

BACKGROUND

The present invention relates to a method of evaluating an optical analysis device and a phantom sample.

Hitherto, an optical analysis device capable of quantitatively observing a state and characteristics of light emitting particles in an aqueous solution having a lower concentration than those dealt with in optical analysis techniques including a statistical process, such as fluorescence correlation spectroscopy (FCS) has been known (for example, International Publication No. WO2011/108369).

This optical analysis device uses an optical system capable of detecting light from a confocal volume in the aqueous solution, as in case of a confocal microscope or a multi-photon excitation microscope. While the position of the confocal volume is moved in the aqueous solution, that is, while the aqueous solution is scanned using the confocal volume, when light emitting particles which are dispersed in the aqueous solution and randomly move are included in the confocal volume, the light emitted from the light emitting particles is detected.

Basically, this optical analysis device measures the concentration of the light emitting particles sufficiently discretely dispersed in the aqueous solution with respect to the size of the confocal volume, and is based on a very plain and simple principle that the pulse sequence of the fluorescence intensity (photon) obtained when the confocal volume scanned at a speed higher than a speed of the diffusion of the particles by Brownian movement of water in the aqueous solution passes through the particle reflects a bell shape which is an intensity distribution of the confocal volume, and this characteristic shape is determined as one particle.

One passing particle is counted as one continuous bell-shaped mountain (peak), and the sum of the number of peaks during a set scanning time is proportional to the concentration of the particles in the aqueous solution. That is, when target particles are previously allowed to exist at a known concentration, the number of peaks during scanning for a set time is measured, and this operation is performed on aqueous solutions having a series of concentrations, the concentration and the number of peaks can be calibrated. As a result, when an aqueous solution having an unknown concentration is subjected to the measurement and the number of peaks thereof is obtained, the concentration can be measured.

When the optical system of the foregoing optical analysis device is evaluated, a plurality of types of aqueous solutions of fluorescent dye molecules having different known concentrations in practice is prepared, and the number of peaks of the fluorescent light obtained when confocal volumes are scanned over a predetermined time in the respective aqueous solutions is associated with the concentration to perform an operation of calibrating the relationship between the number of peaks and the concentration.

At this time, when a state in which the number of peaks obtained with respect to a predetermined concentration is smaller than the number estimated from the optical system, or a state in which the height of the pulse sequence of photons forming the peak is low, i.e., the fluorescent light has a low intensity is confirmed, these indicate that the optical system is not in an accurate state. Here, as elements which determine the state, there are the size of the confocal volume provided in the aqueous solution, the height of the confocal volume from a surface of a transparent bottom plate of the container in which the aqueous solution is held (the position of the focal point), the scanning speed, the sensitivity of the detector, deviation of an optical axis, and the like.

SUMMARY

In order to achieve the above-described object, the invention provides the following means.

An aspect of the invention provides a method of evaluating an optical analysis device including an optical system capable of forming a confocal volume at a focal position by condensing excitation light, the method including the steps of: placing, at the focal position of the optical system, a phantom sample in which two or more types of solid members having different fluorescent substance concentrations are arranged adjacent to each other; irradiating the phantom sample with excitation light through the optical system while relatively moving the confocal volume formed by the optical system and the phantom sample in an arrangement direction of the solid members; detecting fluorescent light generated in the solid members placed in the confocal volume; and evaluating the optical system based on the detected fluorescent light.

According to this aspect, in a state in which the focal position of the optical system of the optical analysis device coincides with the solid member, when the phantom sample and the confocal volume formed by the optical system are relatively moved in the arrangement direction of the solid members, the detected fluorescence intensity is varied stepwise.

When the focal position coincides with the solid member, the fluorescence intensity rapidly varies in a boundary position between the solid members. However, when the focal position does not coincide with the solid member, the fluorescence intensity smoothly varies. Accordingly, by obtaining a slope of the variation in the intensity of the fluorescent light in this position, whether the focal position is appropriate can be easily evaluated. In addition, when the confocal volume is formed to have an appropriate size, the detected fluorescence intensity is high, but when the confocal volume is small, the detected fluorescence intensity is low. Accordingly, using this, whether the size of the confocal volume or detector sensitivity is appropriate can be easily evaluated.

In the above-described aspect, the phantom sample may be provided by alternately arranging first solid members containing a fluorescent substance having a predetermined concentration and second solid members containing no fluorescent substance.

Accordingly, a difference between the intensities of the fluorescent light generated at the boundary between the solid members adjacent to each other can be made marked.

In the above-described aspect, the solid members may be arranged in a constant cycle.

Accordingly, in the relative movement of the confocal volume formed by the optical system and the solid members, these are relatively moved at a constant relative speed, and thus the obtained fluorescence intensity can be varied in a constant cycle. As a result, the relative moving speed, that is, constancy of the scanning speed can be evaluated from the cyclicity of the fluorescence intensity.

In the above-described aspect, the solid members may be linearly arranged.

Accordingly, the above-described evaluation can be performed just by linearly moving the confocal volume formed by the optical system and the solid members in the arrangement direction of the solid members.

In the above-described aspect, the solid members may be arranged in a circumferential direction.

Accordingly, the above-described evaluation can be performed just by rotating the confocal volume formed by the optical system and the solid members around a center of the arrangement of the solid members.

In the above-described aspect, in the step of evaluating the optical system, whether the focal position of the optical system is appropriate may be evaluated based on a slope of a variation in the intensity of the fluorescent light in a position where the different solid members are adjacent to each other.

When the focal position of the optical system accurately coincides with the phantom sample, the intensity of the detected fluorescent light varies stepwise in a position adjacent to the solid members, and thus a slope of the variation is limitlessly large. However, when the focal position is deviated, the slope of the variation in the intensity of the fluorescent light is reduced. Accordingly, whether the focal position of the optical system is appropriate can be easily evaluated by detecting the slope of the variation in the intensity.

In the above-described aspect, in the step of evaluating the optical system, whether a size of the confocal volume or detector sensitivity is appropriate may be evaluated based on the intensity of the detected fluorescent light.

When the size of the confocal volume or the detector sensitivity is appropriate, a predetermined fluorescence intensity can be obtained, and when the size of the confocal volume or the detector sensitivity is not appropriate, a lower fluorescence intensity is obtained. Accordingly, these can be easily evaluated.

In the above-described aspect, in the step of evaluating the optical system, whether a speed of the excitation light scanning by the optical system is appropriate may be evaluated based on a time interval of a variation in the intensity of the fluorescent light in a position where the different solid members are adjacent to each other.

Accordingly, the amount of the fluorescent light generated in the solid members varies stepwise at the boundary between the solid members adjacent to each other, and thus whether the speed of the excitation light scanning by the optical system is appropriate can be easily evaluated by confirming the time interval of the variation.

Another aspect of the invention provides a phantom sample which is used in the method of evaluating an optical analysis device according to any one of the above-described means.

According to this aspect, no great effort is required to prepare an aqueous solution to perform adjustment of an optical analysis device as in the related art. Accordingly, artificial errors do not occur during the preparation, and a fluctuation in the concentration by water evaporation or the like does not also occur even when the concentration is significantly low. In addition, deterioration such as discoloration of fluorescent dye molecules does not occur, and thus excellent preservability is obtained. Therefore, the optical system of the optical analysis device can be easily evaluated with high accuracy.

DETAILED DESCRIPTION

A method of evaluating an optical analysis device and a phantom sample 1 according to an embodiment of the invention will be described with reference to the drawings.

Figure 1:
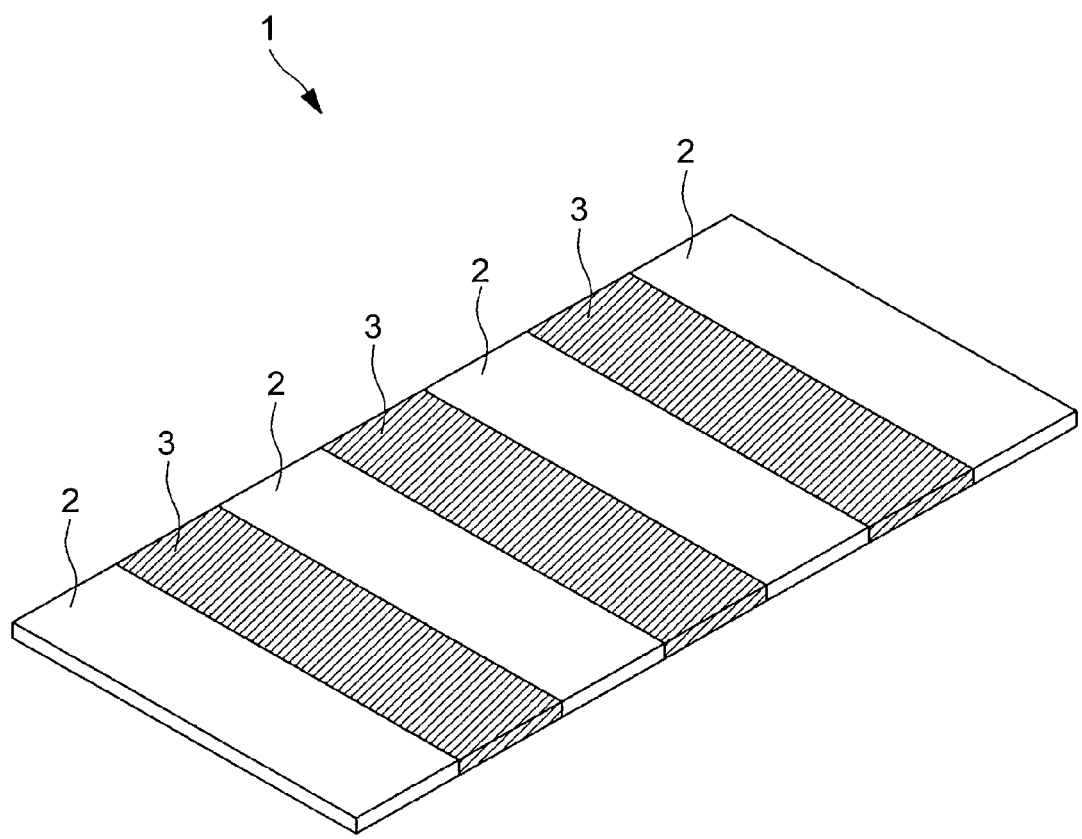
FIG. 1 is a perspective view illustrating a phantom sample according to an embodiment of the invention.

As illustrated in FIG. 1, the phantom sample 1 according to this embodiment is provided to have a flat plate shape by alternately arranging two types of solid members 2 and 3 having different fluorescent substance concentrations adjacent to each other.

One solid member 2 contains a fluorescent substance having a predetermined fluorescence concentration. The other solid member 3 contains no fluorescent substance (contains a fluorescent substance having zero fluorescence concentration). These solid members 2 and 3 are made sufficiently thin and the width dimensions thereof are set to be the same as each other with high accuracy.

Hereinafter, a method of evaluating an optical analysis device using the phantom sample 1 according to this embodiment provided as described above will be described.

Figure 2:
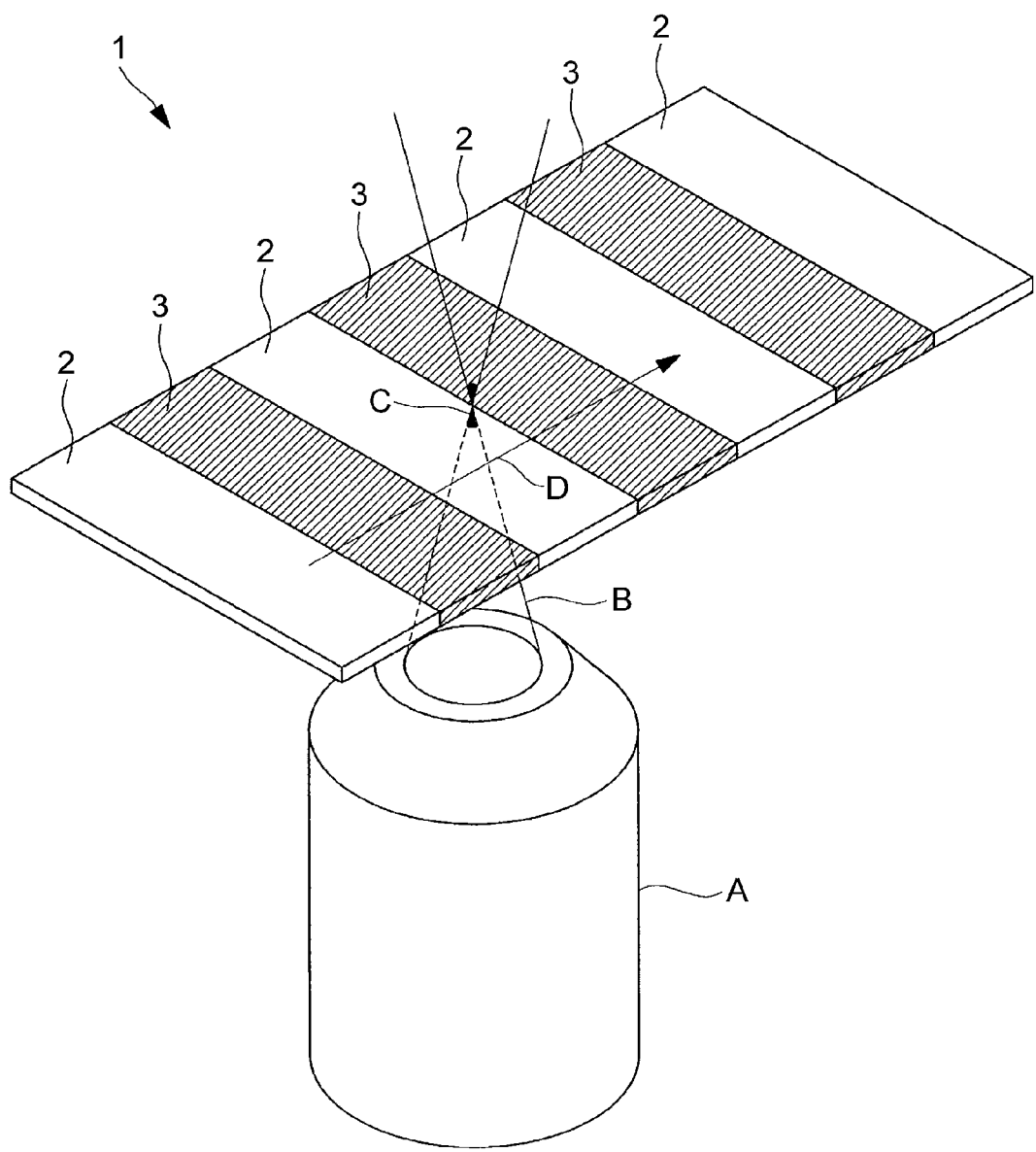
FIG. 2 is a partial perspective view illustrating a method of evaluating an optical analysis device using the phantom sample of FIG. 1.

In order to evaluate an optical analysis device including a confocal optical system or a multi-photon excitation optical system using the phantom sample 1 according to this embodiment, an optical system A of the optical analysis device is adjusted so that a focal position thereof is placed to coincide with the phantom sample 1 as illustrated in FIG. 2.

In this state, the phantom sample 1 is irradiated with excitation light B propagated through the optical system A. Accordingly, a confocal volume C formed at the focal position of the optical system A coincides with the phantom sample 1, the fluorescent substance in the confocal volume C is excited, and thus fluorescent light is generated.

In addition, scanning means (not shown) of the optical analysis device is operated to move the confocal volume C in a direction intersecting with an optical axis and coinciding with the arrangement direction of the solid members 2 and 3 (the direction represented by the arrow D). Accordingly, the confocal volume C is moved relative to the solid members 2 and 3.

The fluorescent light generated in the solid members 2 and 3 is condensed by the optical system A of the optical analysis device and is detected by a light detector (not shown).

That is, while the confocal volume C coincides with one solid member 2 containing a fluorescent substance, fluorescent light is generated in the solid member 2 and a signal having a predetermined intensity is generated from the light detector, and while the confocal volume C coincides with the other solid member 3 containing no fluorescent substance, no signal is generated from the light detector (or a dark noise-level signal is generated). Accordingly, while the confocal volume C and the solid members 2 and 3 relatively move, the signal detected by the light detector varies to draw a rectangular wave.

Figure 3:
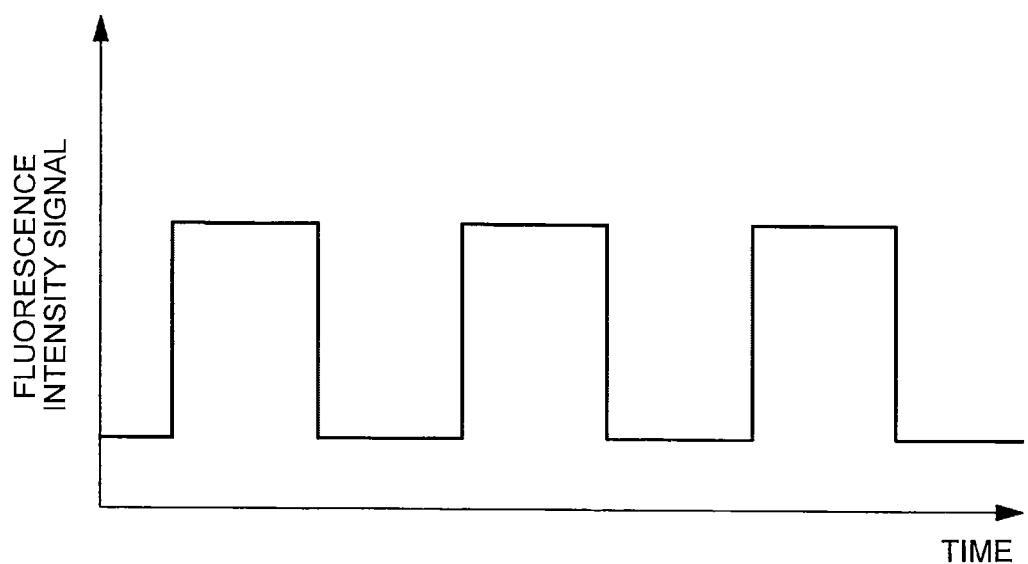
FIG. 3 is a waveform illustrating a variation with time in the fluorescence intensity detected by a light detector when the phantom sample of FIG. 1 coincides with a focal position of an optical system of the optical analysis device.

In this case, when the position of the confocal volume C in the optical axis direction accurately coincides with the solid member 2 or 3, the position where the thinnest confocal volume C is formed is placed to cross the solid member 2 or 3, and thus as shown in FIG. 3, the signal from the light detector at a boundary position between the two types of solid members varies stepwise from zero to a finite value or from the finite value to zero. Accordingly, the slope of the variation with time of the signal at the boundary position between the solid members 2 and 3 approaches infinity.

Figure 4:
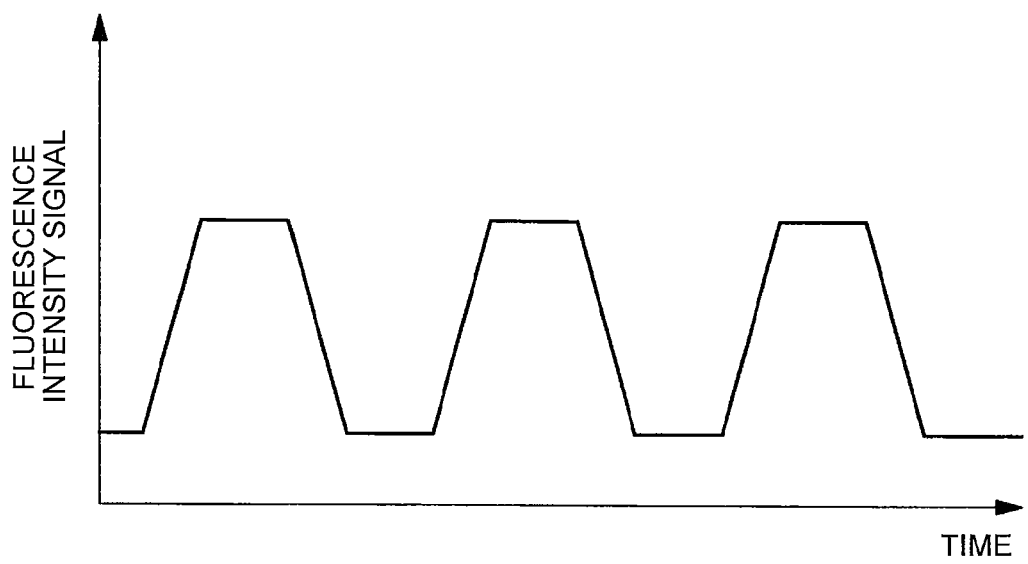
FIG. 4 is a waveform illustrating a variation with time in the fluorescence intensity detected by the light detector when the phantom sample of FIG. 1 does not coincide with the focal position of the optical system of the optical analysis device.

In contrast, when the position of the confocal volume C in the optical axis direction does not accurately coincide with the solid member 2 or 3, the position where the confocal volume C widens is placed to cross the solid member 2 or 3, and thus as shown in FIG. 4, the signal from the light detector at a boundary position between the two types of solid members 2 and 3 smoothly varies. Accordingly, the slope of the variation with time of the signal at the boundary position between the solid members 2 and 3 is reduced.

As a result, according to the phantom sample 1 of this embodiment, there is an advantage in that whether the focal position of the optical system A accurately coincides with the phantom sample 1 can be easily evaluated with a variation with time of the signal of the fluorescence intensity detected by the optical analysis device.

In addition, in the phantom sample 1 according to this embodiment, one solid member 2 has a predetermined fluorescence concentration, and thus the intensity of the fluorescent light generated by irradiation with excitation light having a predetermined intensity is previously known. Accordingly, even when the focal position of the optical system A can be evaluated to accurately coincide with the phantom sample 1 as described above, when the maximum intensity of the signal detected by the light detector is lower than the previously known value, any of whether a light source generating the excitation light B has a problem, whether the size of the confocal volume C is too small, and whether the sensitivity of the light detector is reduced can be easily evaluated.

Furthermore, in the phantom sample 1 according to this embodiment, the two types of solid members 2 and 3 have the same width dimension with high accuracy. Accordingly, when the relative moving speed of the confocal volume C and the solid members 2 and 3 is uniform, the signal generated by the light detector accurately cyclically varies. Accordingly, there is an advantage in that by detecting this cycle, whether the relative moving speed of the confocal volume C and the solid members 2 and 3, that is, the scanning speed of the excitation light B is constant can be easily evaluated.

In this embodiment, the solid members 2 having a predetermined concentration and the solid members 3 having zero concentration are alternately arranged. However, in place of this, both of the solid members 2 and 3 may contain a fluorescent substance and the solid members having distinctly different concentrations may be alternately arranged. Three or more types of solid members having different concentrations may be arranged. The phantom sample 1 having solid members containing different fluorescent substances according to the type of excitation light to be applied may be replaced.

Figure 5:
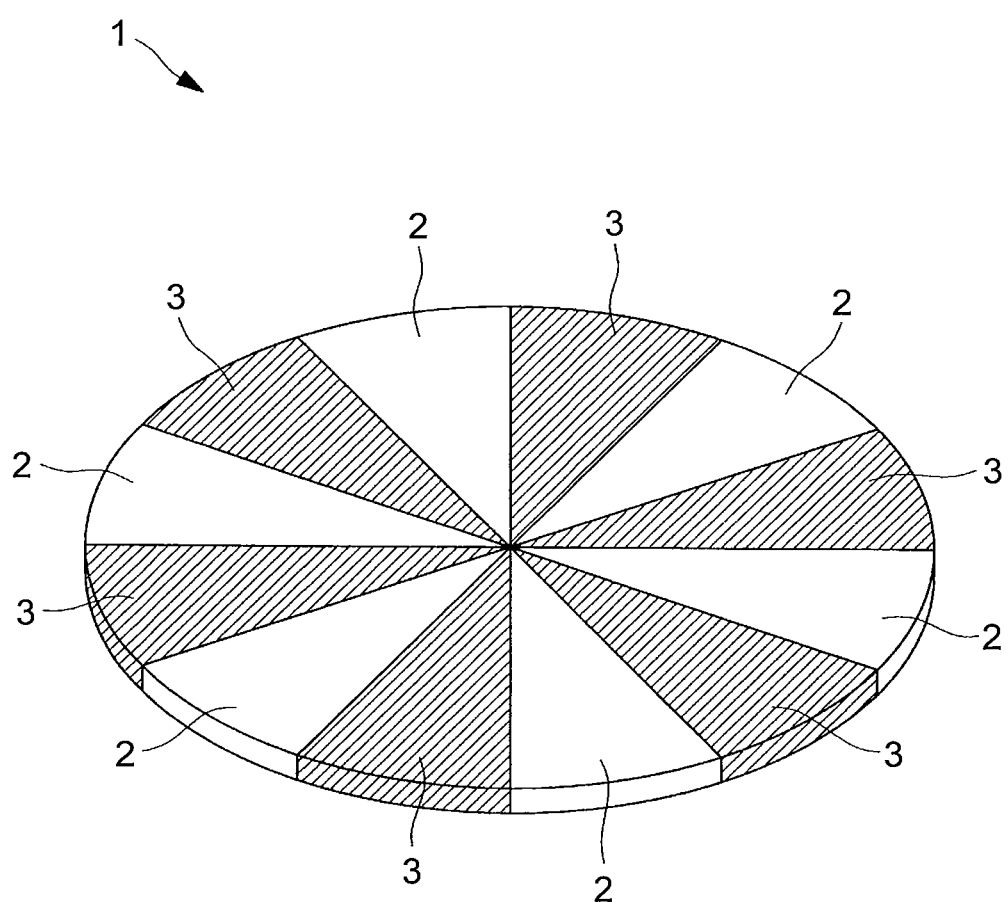
FIG. 5 is a perspective view illustrating a modification example of the phantom sample of FIG. 1.

In addition, in this embodiment, the phantom sample 1 in which the solid members 2 and 3 are linearly arranged is exemplified. However, in place of this, a phantom sample 1 in which fan-shaped solid members 2 and 3 having different fluorescence concentrations are alternately arranged in a circumferential direction so as to form a disc shape as illustrated in FIG. 5 may be employed. Accordingly, the above-described evaluation can be continuously performed just by rotating the phantom sample 1 around a center axis thereof in one direction at a uniform speed.

In addition, in this embodiment, since the solid members 2 and 3 having exactly the same width dimension are arranged, a cyclic output waveform can be obtained at any position as long as relative movement is performed at a uniform speed. However, the invention is not limited thereto. That is, just by considering the variation of the signal at the boundary position between the solid members 2 and 3 adjacent to each other, the cyclicity is not required and the width dimensions may not be the same as each other.

In addition, in case of evaluation content requiring the cyclicity, the width dimension may be different for the different types of solid members 2 and 3. When the width dimensions of the same type of solid members 2 (3) coincide with each other, the cyclicity is maintained. Thus, the scanning speed evaluation can be performed with this.

A system for applying the phantom sample 1 to evaluate the optical analysis device according to an embodiment of the invention will be described.

The system can include one or more processors comprising hardware configured to control a light source for radiating the excitation light, the optical system, the detector and the scanning means. Further, the one or more processors comprising hardware are configured to perform the above-described evaluations of the optical analysis device. The one or more processors comprising hardware includes circuits, integrated circuits, a computer, and a storage device storing instructions that can be executed by the computer.

The system can further include the phantom sample 1.

The system can further include the optical analysis device.

In the above-described embodiments, the optical analysis device can include a light source, an optical system, a detector, and a moving mechanism.

The light source is configured to radiate an excitation light sufficient to excite the fluorescence substance of the solid members 2 (3) to emit fluorescent light. An example of the light source includes a laser.

The detector is configured to detect the fluorescent light generated in the phantom sample. An example of the detector is a photomultiplier tube.

The optical system can include one or more optical structures configured to manipulate the excitation light to form the confocal volume at the focal position that coincides with the phantom sample. The optical system can further include one or more optical structures configured to condense the fluorescent light generated in the phantom sample.

The moving mechanism corresponds to the above-described scanning means. The moving mechanism can include controllable mechanical and electromechanical drive mechanisms that relatively move the confocal volume and the phantom same in a controllable direction and at a controllable speed.

In the above-described embodiments, the optical analysis device can include one or more of the structures described in U.S. Pat. No. 8,710,413, the contents of which is hereby incorporated by reference.

DESCRIPTION OF REFERENCE NUMERALS

1: phantom sample
2, 3: solid member
A: optical system
B: excitation light
C: confocal volume

The invention claimed is:

1. A method of evaluating an optical analysis device including an optical system capable of forming a confocal volume at a focal position by condensing excitation light, the method comprising the steps of:
   placing, at the focal position of the optical system, a phantom sample in which two or more types of solid members having different fluorescent substance concentrations are arranged adjacent to each other;
   irradiating the phantom sample with excitation light through the optical system while relatively moving the confocal volume formed by the optical system and the phantom sample in a same direction of an arrangement of the solid members;
   detecting fluorescent light generated in the solid members placed in the confocal volume; and
   evaluating the optical system based on the detected fluorescent light,
   wherein the step of evaluating the optical system comprises:
      determining a time interval of a variation in the intensity of the fluorescent light in a position where the different solid members are adjacent to each other; and
      evaluating whether a speed of the excitation light scanning by the optical system is appropriate based on the time interval determined.

2. The method of evaluating an optical analysis device according to claim 1,
   wherein the phantom sample is provided by alternately arranging first solid members containing a fluorescent substance having a predetermined concentration and second solid members containing no fluorescent substance.

3. The method of evaluating an optical analysis device according to claim 1,
   wherein the arrangement of the solid members are repeated.

4. The method of evaluating an optical analysis device according to claim 1,
   wherein the solid members are linearly arranged.

5. The method of evaluating an optical analysis device according to claim 1,
   wherein the solid members are arranged in a circumferential direction.

6. The method of evaluating an optical analysis device according to claim 1,
   wherein in the step of evaluating the optical system, whether the focal position of the optical system is appropriate is evaluated based on a slope of the variation in the intensity of the fluorescent light in the position where the different solid members are adjacent to each other.

7. The method of evaluating an optical analysis device according to claim 1,
   wherein in the step of evaluating the optical system, whether a size of the confocal volume or detector sensitivity is appropriate is evaluated based on the intensity of the detected fluorescent light.

8. A phantom sample which is used in the method of evaluating an optical analysis device according to claim 1.

9. A system for applying a phantom sample, the phantom sample comprising two or more types of solid members, having respectively different predetermined fluorescence characteristics, arranged in a predetermined arrangement pattern and in a predetermined arrangement direction, to evaluate an optical analysis device, the optical analysis device comprising:
   a light source configured to radiate an excitation light;
   an optical system configured manipulate the excitation light to form a confocal volume at a focal position that coincides with the phantom sample;
   a detector configured to detect fluorescent light generated in the phantom sample irradiated by the excitation light; and
   a moving mechanism configured to move the phantom sample relative to the confocal volume formed by the optical system,
   wherein the system comprises a processor comprising hardware, the processor being configured to:
      control the light source to irradiate the phantom sample with the excitation light;
      control the moving mechanism to relatively move the confocal volume formed by the optical system and the phantom sample in the predetermined arrangement direction;
      control the detector to detect the fluorescent light generated in the phantom sample irradiated by the excitation light; and
      evaluate the optical system based on the detected fluorescent light,
      wherein evaluating the optical system comprises:
         determining a time interval of a variation in the intensity of the fluorescent light in a position where the different solid members are adjacent to each other; and
         evaluating whether a speed of the excitation light scanning by the optical system is appropriate based on the time interval determined.

10. The system according to claim 9, further comprising the phantom sample,
    wherein the phantom sample comprises first-type solid members having a first predetermined fluorescence characteristic and second-type solid members having a second predetermined fluorescence characteristic, and
    wherein the first-type solid members and the second-type solid members are alternately arranged in the predetermined arrangement direction.

11. The system according to claim 10,
    wherein the first predetermined fluorescence characteristic is a first concentration of a fluorescence substance, and
    wherein the second predetermined fluorescence characteristic is a second concentration of the fluorescence substance, the second concentration being different from the first concentration.

12. The system according to claim 9, further comprising the phantom sample,
wherein the two or more types of solid members are arranged in a repeated pattern.

13. The system according to claim 9, further comprising the phantom sample,
wherein the predetermined arrangement direction is a linear direction.

14. The system according to claim 9, further comprising the phantom sample,
wherein the predetermined arrangement direction is a circumferential direction.

15. The system according to claim 9,
wherein the processor is configured to evaluate the optical system based on the detected fluorescent light by:
determining a slope of a variation of an intensity signal of the fluorescent light detected by the detector at a boundary position between a first type of the solid members and a second type of the solid members, and
determining whether the focal position of the optical system is appropriate based on the determined slope.

16. The system according to claim 9,
wherein the processor is further configured to evaluate the optical system based on the detected fluorescent light by:
determining a result of a comparison of the determined slope with a predetermined value, and
determining whether the focal position of the optical system is appropriate based on the result of the comparison.

17. The system according to claim 9,
wherein the processor is configured to evaluate the optical system based on the detected fluorescent light by:
determining an intensity of the fluorescent light detected by the detector; and
determining whether one or more of an intensity of the excitation light, a size of the confocal volume, and a sensitivity of the detector is appropriate based on the determined intensity.

18. A storage device storing instructions that when executed by a processor comprising hardware, configures the processor to apply a phantom sample, the phantom sample comprising two or more types of solid members, having respectively different predetermined fluorescence characteristics, arranged in a predetermined arrangement pattern and in a predetermined arrangement direction, to evaluate an optical analysis device, the optical analysis device comprising:
a light source configured to radiate an excitation light;
an optical system configured manipulate the excitation light to form a confocal volume at a focal position that coincides with the phantom sample;
a detector configured to detect fluorescent light generated in the phantom sample irradiated by the excitation light; and
a moving mechanism configured to move the phantom sample relative to the confocal volume formed by the optical system,
wherein the instructions configure the processor to:
control the light source to irradiate the phantom sample with the excitation light;
control the moving mechanism to relatively move the confocal volume formed by the optical system and the phantom sample in the predetermined arrangement direction;
control the detector to detect the fluorescent light generated in the phantom sample irradiated by the excitation light; and
evaluate the optical system based on the detected fluorescent light,
wherein evaluating the optical system comprises:
determining a time interval of a variation in the intensity of the fluorescent light in a position where the different solid members are adjacent to each other; and
evaluating whether a speed of the excitation light scanning by the optical system is appropriate based on the time interval determined.

19. A method for applying a phantom sample, the phantom sample comprising two or more types of solid members, having respectively different predetermined fluorescence characteristics, arranged in a predetermined arrangement pattern and in a predetermined arrangement direction, to evaluate an optical analysis device, the optical analysis device comprising:
a light source configured to radiate an excitation light;
an optical system configured manipulate the excitation light to form a confocal volume at a focal position that coincides with the phantom sample;
a detector configured to detect fluorescent light generated in the phantom sample irradiated by the excitation light; and
a moving mechanism configured to move the phantom sample relative to the confocal volume formed by the optical system,
wherein the method comprises:
controlling the light source to irradiate the phantom sample with the excitation light; controlling the moving mechanism to relatively move the confocal volume formed by the optical system and the phantom sample in the predetermined arrangement direction;
controlling the detector to detect the fluorescent light generated in the phantom sample irradiated by the excitation light; and
evaluating the optical system based on the detected fluorescent light,
wherein evaluating the optical system comprises:
determining a time interval of a variation in the intensity of the fluorescent light in a position where the different solid members are adjacent to each other; and
evaluating whether a speed of the excitation light scanning by the optical system is appropriate based on the time interval determined.

* * * * *